US008435558B1

(12) United States Patent
Hood et al.

(10) Patent No.: US 8,435,558 B1
(45) Date of Patent: *May 7, 2013

(54) ULTRASOUND ENHANCEMENT OF DRUG RELEASE ACROSS NON-IONIC SURFACTANT MEMBRANES

(75) Inventors: Elizabeth Hood, Philadelphia, PA (US); Joel A. Strom, Tampa, FL (US); Michael VanAuker, Santa Clara, CA (US)

(73) Assignee: University of South Florida, Tampa, FL (US)

( * ) Notice: Subject to any disclaimer, the term of this patent is extended or adjusted under 35 U.S.C. 154(b) by 174 days.

This patent is subject to a terminal disclaimer.

(21) Appl. No.: 13/185,100

(22) Filed: Jul. 18, 2011

Related U.S. Application Data (63) Continuation-in-part of application No. 11/427,034, filed on Jun. 28, 2006, now Pat. No. 7,981,442.

(60) Provisional application No. 60/695,484, filed on Jun. 28, 2005.

(51) Int. Cl.
*A61K 9/127* (2006.01)
*A61K 9/48* (2006.01)

(52) U.S. Cl.
USPC ........ 424/450; 424/78.03; 424/401; 424/486; 424/489; 514/2; 514/44

(58) Field of Classification Search ................. 424/9.51, 424/9.52, 450, 465, 489; 514/2, 44, 537; 210/649–652, 646, 204, 152
See application file for complete search history.

(56) References Cited

U.S. PATENT DOCUMENTS

| | | | |
|---|---|---|---|
| 4,780,212 A * | 10/1988 | Kost et al. ..................... | 210/646 |
| 5,580,575 A | 12/1996 | Unger et al. | |
| 6,403,056 B1 | 6/2002 | Unger | |
| 6,623,430 B1 | 9/2003 | Slayton et al. | |
| 6,884,407 B1 | 4/2005 | Unger | |
| 7,169,382 B2 * | 1/2007 | Chopart et al. ............ | 424/78.03 |
| 2002/0159951 A1 | 10/2002 | Unger et al. | |
| 2003/0064097 A1 | 4/2003 | Patel et al. | |
| 2003/0157025 A1 | 8/2003 | Unger et al. | |
| 2005/0019266 A1 | 1/2005 | Unger et al. | |
| 2007/0172520 A1 | 7/2007 | VanAuker et al. | |

OTHER PUBLICATIONS

Crowder et al., Sonic Activation of Molecularly-Targeted Nanoparticles Accelerates Transmembrane Lipid Delivery to Cancer Cells Through Contact-Mediated Mechanisms: Implications for Enhanced Local Drug Delivery, Ultrasound in Med. & Biol., 2005, vol. 31, No. 12, pp. 1693-1700.
Mitragotri, Healing Sound: The Use of Ultrasound in Drug Delivery and Other Therapeutic Applications, Nature Reviews, 2005, vol. 4, pp. 255-260.
Unger et al., Local Drug and Gene Delivery Through Microbubbles, Progress in Cardiovascular Diseases, 2001, vol. 44, No. 1, pp. 45-54.
Tachibana et al., Albumin Microbubble Echo-Contrast Material as an Enhancer for Ultrasound Accelerated Thrombolysis, Circulation, 1995, vol. 92, pp. 1148-1150.
Hamilton et al., Intravascular Ultrasound Molecular Imaging of Atheroma Components In Vivo, Journal of American College of Cardiology, 2004, vol. 43, No. 3, pp. 453-460.
Tiukinhoy et al., Novel Echogenic Drug-Immunoliposomes for Drug Delivery, Investigative Radiology, 2004, vol. 39, No. 2, pp. 104-110.
Price et al., Contrast Ultrasound Targeted Drug and Gene Delivery: An Update on a New Therapeutic Modality, J. Cardiovasc Pharmacol. Therapeut., 2002, vol. 7, No. 3, pp. 171-180.
Villanueva et al., Microbubbles Targeted to Intercellular Adhesion Molecule-1 Bind to Activated Coronary Artery Endothelial Cells, Circulation, 1998,vol. 98, pp. 1-5.
Unger et al., Therapeutic Applications of Lipid-Coated Microbubbles, Advanced Drug Delivery Reviews, 2004, vol. 56, pp. 1291-1314.
Uchegbu et al., Non-Ionic Surfactant Based Vesicles (Niosomes) in Drug Delivery, International Journal of Pharmaceutics, 1998, vol. 172, pp. 33-70.
Ng et al., Therapeutic Ultrasound: Its Application in Drug Delivery, Medicinal Research Reviews, 2002, vol. 22, No. 2, pp. 204-223.
Hood et al., Ultrasound Enhancement of Drug Release Across Non Ionic Surfactant Vesicle Membranes, Proceedings of the 26th Annual International Conference of the IEEE EMBS, San Francisco, CA, Sep. 1-5, 2004, pp. 3527-3530.
Lasic, Liposomes: From Physics to Applications, Amsterdam, Netherlands: Elsevier, 1993, pp. 31-32.
Uchegbu et al., Non-Ionic Surfactant Vesicles (Niosomes): Physical and Pharmaceutical Chemistry, Advances in Colloid and Interface Science, 1995, vol. 58, pp. 1-55.
Bangham et al., Diffusion of Univalent Ions Across the Lamellae of Swollen Phospholipids, J. Mol. Biol., 1965, vol. 13, pp. 238-252.
Lin et al., PEG-Lipids and Oligo (ethylene glycol) Surfactants Enhance the Ultrasonic Permeabilizability of Liposomes, Langmuir, 2003, vol. 19, pp. 1098-1105.

(Continued)

*Primary Examiner* — Michael G Hartley
*Assistant Examiner* — Jagadishwar Samala
(74) *Attorney, Agent, or Firm* — Michele L. Lawson; Smith & Hopen, P.A.

(57) ABSTRACT

A method of targeted drug delivery and imaging using non-ionic surfactant vesicles (niosomes) in combination with ultrasound is presented. Niosomes have potential applications in targeted drug delivery and imaging because of their ability to encapsulate therapeutic agents and their enhanced uptake by physiological membranes. The niosomes may be administered to the subject via catheter. Ultrasound may be used to mediate delivery non-invasively by altering the niosome membrane structure. Niosomes composed of polyoxyethylene sorbitan monostearate (Tween 61), cholesterol, and dicetyl phosphate were synthesized via a thin film hydration technique and used for encapsulation studies. Carboxyfluorescein dye (CF) was used as a drug model to demonstrate delivery. The amount of dye in the niosomes, the concentration of the vesicles, and their mean particle size after each 5 minute incremental exposure to ultrasound was monitored. It was found that ultrasound at specific frequencies can reversibly permeabilize the lipid membrane of niosomes to allow the controlled release of a compound without destroying the niosome structure.

16 Claims, 5 Drawing Sheets

OTHER PUBLICATIONS

Manosroi et al., Characterization of Vesicles Prepared with Various Non-Ionic Surfactants Mixed with Cholesterol, Colloids and Surfaces B: Biointerfaces, 2003, vol. 30, pp. 129-138.

Namdeo et al., Niosomal Delivery of 5-fluorouracil, J. Microencapsulation, 1999, vol. 16, No. 6, pp. 731-740.

Rapoport et al., Ultrasound-triggered Drug Targeting of Tumors in Vitro and In Vivo, Ultrasonics, 2004, vol. 42, pp. 943-950.

Gopinath et al., Pharmacokinetics of Zidovudine Following Intravenous Bolus Administration of a Novel Niosome Preparation Devoid of Cholesterol, Arzneim.-Forsch./Drug Res., 2001, vol. 51 (II), pp. 924-930.

Jain et al., Preparation and Characterization of Niosomes Containing Rifampicin for Lung Targeting, J. Microencapsulation, 1995, vol. 12, No. 4, pp. 401-407.

Baillie et al., Non-Ionic Surfactant Vesicles, Niosomes, as a Delivery System for the Anti-leishmanial Drug, Sodium Stibogluconate, J. Pharm. Pharmacol., 1986, vol. 38, pp. 502-505.

Azmin et al., The Effect of Non-Ionic Surfactant Vesicle(Niosome) Entrapment on the Absorption and Distribution of Methotrexate in Mice, J. Pharm. Pharmacol., 1985, vol. 37, pp. 237-242.

Baillie et al., The Preparation and Properties of Niosomes-Non-Ionic Surfactant Vesicles, J. Pharm. Pharmacol., 1985, vol. 37, pp. 863-868.

Hood et al., Entrapment Efficiency and Membrane Permeability of Non Ionic Surfactant Vesicles, Proc. 2003 AIChE Annual Conference, Nov. 16-21, 2003, San Francisco, CA.

* cited by examiner

ULTRASOUND ENHANCEMENT OF DRUG RELEASE ACROSS NON-IONIC SURFACTANT MEMBRANES

CROSS REFERENCE TO RELATED APPLICATIONS

This application is a continuation-in-part application which claims priority to currently pending U.S. patent application Ser. No. 11/427,034, entitled, "Ultrasound Enhancement of Drug Release Across Non-Ionic Surfactant Membranes", filed Jun. 28, 2006, which claims priority to U.S. Provisional Patent Application 60/695,484, entitled, "Ultrasound Enhancement of Drug Release Across Non-Ionic Surfactant Membranes", filed Jun. 28, 2005, the contents of which are herein incorporated by reference.

FIELD OF INVENTION

This invention relates to the field of therapeutic drug delivery. More specifically, this invention relates to the use of catheters to administer niosomes comprising therapeutic compounds delivered to a targeted region of a patient using ultrasound.

BACKGROUND OF THE INVENTION

Drug delivery systems are developed to lower therapeutic doses, increase residence time, and prolong release over time of drugs to targeted tissues. Toxic effects of drugs can be minimized when uptake by untargeted organs is reduced. Targeting allows delivery of relatively high levels of drug to a focal site, minimizing systemic complications and lowering costs of therapy. Liposomes are self assembly vesicles made from phospholipids and cholesterol that have been widely used in targeted drug delivery applications including cancer therapy, gene delivery, and thrombolysis (Lasic, D. D., *Liposomes: From Physics to Applications*. Amsterdam, the Netherlands: Elsevier, 1993, pp 31-32.) since their discovery almost forty years ago (Bangham, A. D. et al., "Diffusion of univalent ions across the lamellae of swollen phospholipids," J. Mol. Bio. vol. 13, pp. 238-252, 1965.). Vesicles made from synthetic non ionic surfactants (niosomes) are analogous to liposomes. Niosomes have also been used as drug encapsulating vesicles showing advantages over liposomes, including greater chemical stability, lower cost, easier storage and handling, and less potential for toxicity (Uchegbu, I. F. et al., "Non-ionic surfactant vesicles (niosomes): physical and pharmaceutical chemistry." Adv. Colliod. Interfac., vol. 58, no. 1, pp. 1-55, 1995.). As drug delivery vesicles, niosomes have been shown to enhance absorption of some drugs across cell membranes (Lasic, D. D., 1993, pp 31-32), to localize in targeted organs (Jain, C. P. et al., "Preparation and characterization of niosomes containing rifampicin for lung targeting," Microencapsulation, vol. 12 no. 4, pp. 401-407, 1995; Namdeo, A. J. et al., "Niosomal delivery of 5-fluoruoracil," J. Microencapsulation, vol. 16, no. 6, pp. 731-740, 1999.) and tissues (Baille, A. J. et al., "Non-ionic surfactant vesicles, niosomes, as delivery system for the anti-leishmanial drug, sodium stribogluconate," J. Pharm. Pharacol., vol. 38, pp. 502-505, 1986; Azmin, M. N., et al., "The effect of non-ionic surfactant vesicle (niosome) entrapment on the absorption and distribution of methotrexate in mice," J. Pharm. Pharmacol., vol. 37, pp. 237-242, 1985.), and to elude the reticuloendothelial system (Gopinath, D. et al., "Pharmocokinetics of zidovudine following intravenous bolus administration of a novel niosome preparation devoid of cholesterol," A. F. Drug Research, vol. 51, no. 11, pp. 924-930. November, 2001).

The administration of small molecules such as liposomes or niosomes to a subject can occur in a variety of ways including by catheter. Catheters are generally devices that can be inserted into a subject, particularly within tubular structures such as blood vessels, the digestive tract, the urinary tract, the reproductive tract, etc. The general structure of a catheter is well known in the art. A catheter generally has a tubular main body that is flexible and has at least one lumen extending therethrough. A port may be located at one end of the catheter for injection of vesicles such as niosomes into the subject. Attaching an ultrasound imaging probe to a catheter has the advantage of allowing the visualization of the interior walls of a tubular structure of a subject in order to provide guided and targeted delivery of a small molecule, such as a niosome containing a therapeutic or diagnostic compound, to a specific area of the subject Immunoniosomes, such as those described in U.S. Published Patent Application No. 2007/0172520 herein incorporated by reference, may be used to induce an antibody/ligand reaction to allow the niosome to adhere to specific target cells. As defined in the above referenced U.S. Patent Application, immunoniosomes are defined as a niosome bearing an antibody or antibody fragment that acts as a targeting moiety enabling the niosome to specifically bind to a particular target molecule that may exist in solution or may be bound to the surface of a cell.

Ultrasound enhanced drug delivery has several important advantages in that it is noninvasive, can be carefully focused and controlled and can penetrate deep into the body. Early uses of ultrasound to aid drug delivery were transcutaneous. The technique for using ultrasound to drive drug molecules across the percutaneous barrier to a targeted area, or 'phonophoresis', was developed fifty years ago, and is itself a field of research (Ng, K. et al., "Therapeutic ultrasound: its application in drug delivery," Med. Res. Rev., vol. 22, no. 2, pp. 204-223, 2002.). Other drug therapies shown to be enhanced by ultrasound include chemotherapy, thrombolytics, and gene delivery. Drug targeting and localized release has been shown to enhance uptake by tumor cells when encapsulated by polymeric micelles subjected to focused ultrasound at therapeutic levels (Rapoport, N. Y. et al., "Ultrasound-triggered drug targeting of tumors in vitro and in vivo," Ultrasonics, vol. 42, pp. 943-950, 2004). Low intensity ultrasound has been shown to enhance the permeabilization of liposomes with polyethylene glycol head groups (Lin, H. Y. et al., "PEG-Lipids and oligo(ethylene glycol) surfactants enhance the ultrasonic permeabilizability of liposomes," Langmuir, vol. 19, pp. 1098-1105, 2003; Baillie, A. J., et al., "The preparation and properties of niosome—non-ionic surfactant vesicles," J. Pharm. Pharmacol., vol. 37, pp. 863-868, 1985.).

Effective targeted drug delivery can be achieved in many instances through release of therapeutic agents in a more controlled manner than possible with passive diffusion across a bilayer membrane. Controlled release of a drug from a specifically targeted vesicle to a site using ultrasound can be optimized through the tuning of transducer frequency, beam distance and focus, and absolute and peak power delivered to the vesicle suspension. The lipid bilayers that make up liposomes and niosomes are similar to biological membranes in that they are able to self-repair when perturbed. Sonication is widely used to reduce large multilamellar vesicles to smaller unilamellar ones. Control of membrane permeability via ultrasound would have many therapeutic applications especially when coupled with the active and passive drug targeting possible with lipid membrane vesicles. To this end, a technique for making non ionic surfactant vesicles and the use and effect of exposure to clinical levels of ultrasound to achieve release of the drug model is taught herein.

SUMMARY OF INVENTION

The present invention provides a method for the targeted delivery of a pharmaceutical compound to a region of a patient. The method includes the steps of providing a niosome containing the compound, administering an effective amount of the niosome to the patient through a catheter and inducing the dispersion of the niosome membrane using ultrasound to release the compound in the targeted region to achieve therapeutic effect.

In one aspect of the present invention there is a catheter equipped with an ultrasound imaging probe that is sized to fit into a tubular structure such as a blood vessel. The catheter has at least one port for injection of the niosomes. The ultrasound imaging probe provides detailed imaging of the interior surfaces of the tubular structure, allowing for visualization of any area of interest which allows for the guided delivery of the niosomes.

In one example, an intravascular ultrasound imaging probe is used to provide detailed imaging of the interior surfaces of a blood vessel which allows for visualization of atherosclerotic plaques. Visualization of the atherosclerotic plaque by use of intravascular ultrasound allows for guided delivery of the niosome. In use, when a plaque is found, the niosomes are injected through the port and into the subject. This allows for the targeted delivery of a high concentration of the niosome particles to a focused site. This targeted delivery improves uptake relative to similar particles that are delivered through the intravenous injection. The injected niosomes can then adhere to the diseased endothelium by the use of an antibody/ligand interaction. After adhesion, the ultrasound frequency is adjusted to facilitate release of drug at the location of the plaque. This method of delivery reduces the number of doses required for efficacy relative to intravenous or oral administration with non-specific uptake.

In a certain aspect, the method can include the step of monitoring the niosomes using ultrasound to determine the presence of the niosome in the target region. The compound can be a therapeutic compound or a diagnostic compound. In certain aspect of the invention the niosome comprises polyoxyethylene sorbitan monostearate (Tween 61), cholesterol and dicetyl phosphate. The polyoxyethylene sorbitan monostearate (Tween 61) and the cholesterol can be present in about equimolar combination. The niosome can be synthesized using a thin film hydration methodology.

BRIEF DESCRIPTION OF THE DRAWINGS

For a fuller understanding of the invention, reference should be made to the following detailed description, taken in connection with the accompanying drawings, in which.

DETAILED DESCRIPTION OF THE PREFERRED EMBODIMENT

In the following detailed description of the preferred embodiments, reference is made to the accompanying drawings, which form a part hereof, and within which are shown by way of illustration specific embodiments by which the invention may be practiced. It is to be understood that other embodiments may be utilized and structural changes may be made without departing from the scope of the invention.

The terms "substantially non-destructive" as used herein refer to the majority of the lipid membrane of the niosomes remaining intact during the release of the compound from the internal cavity of the niosome. Preferably, the majority of the niosome remaining intact can be 90% or greater including all percentages, rounded to the nearest hundredth of a percent, between 90% and 99.99%. In an embodiment, the majority of the niosome remaining intact can be 80% or greater, to the nearest hundredth of a percent, including all percentages between 80% and 99.99%. In an embodiment, the majority of the niosome remaining intact can be 70% or greater, to the nearest hundredth of a percent, including all percentages between 70% and 99.99%. In an embodiment, the majority of the niosome remaining intact can be 60% or greater, to the nearest hundredth of a percent, including all percentages between 60% and 99.99%. As used in this context, the term "substantially" refers to enough of the niosome remaining intact and containing the desired compound, in the example presented herein this compound is CF dye, to be counted in particle size distributions according to the methods of the invention. As used in this context, "non-destructive" refers to the reversible permeabilization of the lipid membrane of a niosome whereby the contents of the niosome may be released without the decimation of the niosome structure.

The terms "controlled release" as used herein refer to the release of the contents of the niosomes of the present invention being released in a controlled manner through a partial disruption of the lipid membrane of the niosomes. Ultrasound is used to effectuate the controlled release of the compound from the interior of the niosome by reversibly permeabilizing the lipid membrane of the niosome. The release is controlled since neither the lipid membrane nor the niosome itself is destroyed thus the contents of the niosome are not flooded into the targeted area but rather released slowly into the target area.

The term "about" or "approximately" as used herein refers to being within an acceptable error range for the particular value as determined by one of ordinary skill in the art, which will depend in part on how the value is measured or determined, i.e. the limitations of the measurement system, i.e. the degree of precision required for a particular purpose, such as a pharmaceutical formulation. For example, "about" can mean within 1 or more than 1 standard deviation, per the practice in the art. Alternatively, "about" can mean a range of up to 20%, preferably up to 10%, more preferably up to 5% and more preferably still up to 1% of a given value. Alternatively, particularly with respect to biological systems or processes, the term can mean within an order of magnitude, preferably within 5-fold, and more preferably within 2-fold, of a value. Where particular values are described in the application and claims, unless otherwise stated, the term "about" meaning within an acceptable error range for the particular value should be assumed.

Amounts, ultrasound frequencies, and other numerical data may be expressed or presented herein in a range format. It is to be understood that such a range format is used merely for convenience and brevity and thus should be interpreted flexibly to include not only the numerical values explicitly recited as the limits of the range, but also to include all the individual numerical values or sub-ranges encompassed within that range as if each numerical value and sub-range is explicitly recited. As an illustration, a numerical range of "about 1 to about 5" should be interpreted to include not only the explicitly recited values of about 1 to about 5, but also include the individual values and sub-ranges within the indicated range. Thus, included in this numerical range are individual values such as 2, 3, and 4 and sub-ranges such as from 1-3, from 2-4 and from 3-5, etc. This same principle applies to ranges reciting only one numerical value. Furthermore, such an interpretation should apply regardless of the range or the characteristics being described. Where a range of values is provided, it is understood that each intervening value, to the tenth of the unit of the lower limit, unless the context clearly dictates otherwise, between the upper and lower limits of that range is also specifically disclosed. Each smaller range between any stated value or intervening value in a stated range and any other stated or intervening value in that stated range is encompassed in the invention. The upper and lower limits of these smaller ranges may independently be excluded or included within the range. Each range where either, neither, or both limits are included in the smaller ranges are also encompassed by the invention, subject to any specifically excluded limit in the stated range. Where the stated range includes one or both of the limits, ranges excluding either or both of those excluded limits are also included in the invention.

The ultrasound frequency that may be used in the present invention ranges from about 1 MHz to about 55 MHz, including all frequencies included therebetween. In an embodiment of the invention, the ultrasound frequency may range from about 4 MHz to about 55 MHz. In an embodiment, any frequency above 4 MHz may be used. Clinical levels of ultrasound as used in the present invention are known to include all frequencies between about 1 MHz and about 55 MHz.

The exposure to ultrasound can range from 1 minute to upwards of 20 minutes. In an embodiment, the niosomes were exposed to ultrasound in 5 minute increments for 15 minutes.

The niosomes used in the present invention can range in size from 0.025 μm to greater than 10 μm. In an example, the niosomes range from a mean particle size of about 0.89 μm to about 1.05 μm.

A method of targeted drug delivery and imaging using nonionic surfactant vesicles (niosomes) in combination with ultrasound is presented. Niosomes have potential applications in targeted drug delivery and imaging because of their ability to encapsulate therapeutic agents and their enhanced uptake by physiological membranes.

The niosomes of the present invention may be administered to a subject in a variety of ways including through the use of a catheter or probe system. The catheter system may include at least one port for niosome delivery. The at least one port is of sufficient diameter to allow the delivery of the niosomes from the catheter into the subject. The catheter may include a flexible main tubular body in which at least one lumen extends therethrough. The catheter may alternatively contain a flexible outer tubular body and an inner tubular body. The catheter is preferably smooth and manufactured of a biocompatible material. Examples of suitable biocompatible materials include, but are not limited to, polyurethane, polyamide, polyester polyamide resin, polyether polyamide resin, and silicone. The main tubular body of the catheter is of sufficient diameter so as to allow the insertion into various areas of the body of a subject such as blood vessels and to allow the passage of niosomes, liposomes, or other small molecules into the subject.

The catheter may be equipped with an ultrasound imaging probe. The ultrasound imaging probe may be used to visualize the delivery of the niosomes to the desired location. The niosome delivery system including the catheter and ultrasound imaging probe may be used to administer drugs or other small molecules encapsulated in the niosome to a targeted site in order to treat a variety of disorders.

One example for the use of the niosome delivery system is in treating atherosclerotic plaques within blood vessels. In this example, the ultrasound imaging probe and catheter are used intravascularly. Intravascular ultrasound provides detailed imaging of the interior surfaces of the blood vessel wall, allowing for visualization of an atherosclerotic plaque. This visualization allows for guided delivery of the niosome. In operation, when a plaque is found, the niosomes are injected through the port of the catheter thus allowing for the targeted delivery of a high concentration of the niosomes to a focused site. The targeted delivery of the niosomes improves their uptake relative to similar particles that are delivered through an intravenous injection. Once injected, the niosomes can adhere to the diseased endothelium by the use of an antibody/ligand interaction. After adhesion, the ultrasound frequency will be adjusted to facilitate release of drug at the location of the plaque. This targeted drug release at the site of the plaque reduces the number of doses required for efficacy relative to intravenous or oral administration with non-specific uptake.

Ultrasound may be used to mediate delivery non-invasively by altering the niosome membrane structure. Niosomes composed of polyoxyethylene sorbitan monostearate (Tween 61), cholesterol, and dicetyl phosphate were synthesized via a thin film hydration technique and used for encapsulation studies. Carboxyfluorescein dye (CF) was used as a drug model to demonstrate delivery. The amount of dye in the niosomes, the concentration of the vesicles, and their mean particle size after each 5 minute incremental exposure to ultrasound was monitored. Dye concentration in niosome samples decreased while the population and size distribution of the niosome remained largely unchanged. Ultrasound is demonstrated to enhance the rate of dye diffusion across the niosome membrane non-destructively.

Methods

Niosomes were synthesized using a thin film hydration technique (Baillie, A. J., et al., "The preparation and properties of niosome—non-ionic surfactant vesicles," J. Pharm. Pharmacol., vol. 37, pp. 863-868, 1985.) with the surfactant polyoxyethylene sorbitan monostearate (Tween 61), cholesterol, and dicetyl phosphate (DCP) in a 1.00:1.00:0.105 molar ratio. The capability of niosomes of made from several different sorbitan monoesters (Span 20, 40, 60) has been studied and the ability of each to encapsulate a fluorescent dye, 5(6)-carboxyfluorescein (CF) used as a drug model has been evaluated (Hood, E. et al., "Entrapment efficiency and membrane permeability of non ionic surfactant vesicles," in Proc. 2003 AIChE Annual Conference Proceeding CD-ROM, San Francisco, Calif.). The surfactant Tween 61 is similar to Span 60, sharing a common stearyl chain tail group ($C_{18}$) but having more highly hydrated polyoxyethylene (PEO) groups on the hydrophilic group. Tween 61, in equimolar combination with cholesterol, has been reported to have greater encapsulation capabilities of aqueous solutions, and greater stealth in vivo due to the high level of hydration on the vesicle surface (Manosroi, A. et al., "Characterization of vesicles prepared with various non-ionic surfactants mixed with cholesterol." Colliod Surface B, vol. 30, pp. 129-138, 2003.). Niosomes were synthesized using a thin film hydration method followed by sonication. Once the thin films were hydrated in a 5.0 mM CF solution the niosomes were separated from the unencapsulated dye and any unformed lipids or micelles using gel exclusion chromatography with an Amersham ÅKTAprime™ fraction collection system with UV monitoring coupled with a 120 ml column filled with Sephadex G50. In this process, the niosome sample is passed through a column packed with porous gel beads of a uniform pore size (Sephadex G50 pore size 50 nm) using phosphate buffer solution (PBS) as the carrier liquid. The larger vesicle particles fall through the voids and are eluted early while the smaller particles such as unencapsulated dye and unformed lipids are caught up in the pores of the beads, traveling through the column more slowly. This technique allows sample separation into fractions by particle size.

Niosome Characterization Methods

Niosome particle analysis included light scattering, single particle optical sensing technology, optical microscopy, and fluorescence measurements. Fluorescence changes were measured to evaluate encapsulation by the vesicles and leakage of dye from the vesicles over time. Mean particle size and concentration of the niosome vesicles was determined by light scattering and light obstruction techniques using a Particle Sizing Systems Accusizer 780™ with a lower diameter detection limit of 0.57 nm. The entrapment capability and membrane permeability were measured by disrupting the vesicles with Triton X 100, a non-fluorescing surfactant, and quantifying the signal change before and after vesicle breaking using a Perkin Elmer™ spectrometer. Entrapment of CF was determined using fluorescence absorbance correlated to a standard curve of concentration versus intensity. Initial readings of niosome solutions are described as background intensities in this discussion, and final readings include the CF released from the lysed niosomes. The difference of the two gives the dye entrapped in the niosome suspensions. All readings are related to the calibration curve and are reported in moles of CF.

Experimental Methods

Niosome suspensions of mean particle size 0.89 μm and 1.05 μm were subjected to 5 minute increments of ultrasound, with a sample of each left unperturbed as a control. An Acuson Aspen™ echocardiography machine coupled to a 4V2c transducer delivered ultrasound to static suspensions of several ml for each sample. Machine settings were kept constant throughout the experiment with the frequency set to 3.5 MHz, the dynamic range set to 70 dB, and the initial gain set to 10 dB. The spatial peak temporal average was 46 mW/cm$^2$, and the total absolute power was 65 mW.

Fluorescence readings of the niosomes and suspending fluid were obtained at 5 min increments over 15 minutes of ultrasound exposure. All vesicle characterization measurements were repeated three times.

Results

Figure 1:
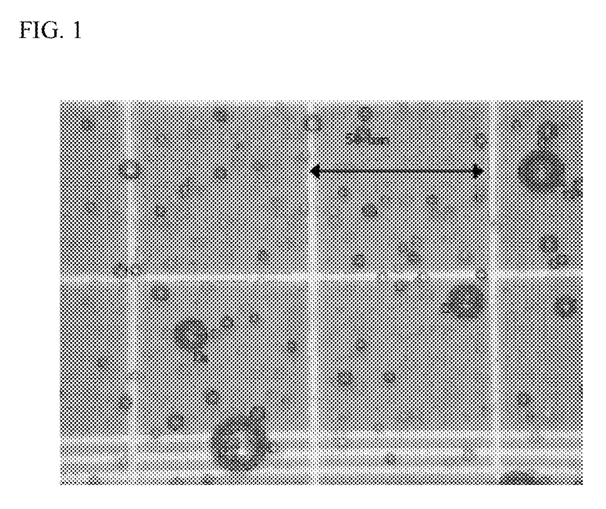
FIG. 1 is a micrograph of a niosome sample on a hemocytometer. Arrow length indicates 50 μm.
Figure 2:
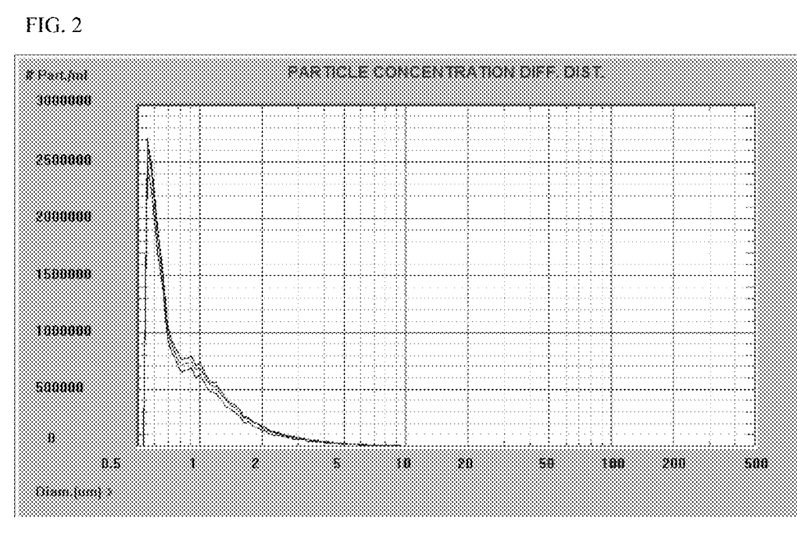
FIG. 2 is a graph illustrating particle size distributions of the 1.05 μm control sample over the duration of the experiment. Upper line plot=0 min, middle line plot=5 min, lower line plot=10 min and 15 mins (note that plots for 10 and 15 mins are superimposed and not distinguishable in the graph).

Vesicle formation is verified using light microscopy as shown in FIG. 1. The graph shown in FIG. 2. represents the particle size distributions (PSD) of the control samples over the duration of the experiment. The CF in the control samples remained unchanged over the duration of the experiment.

Figure 3:
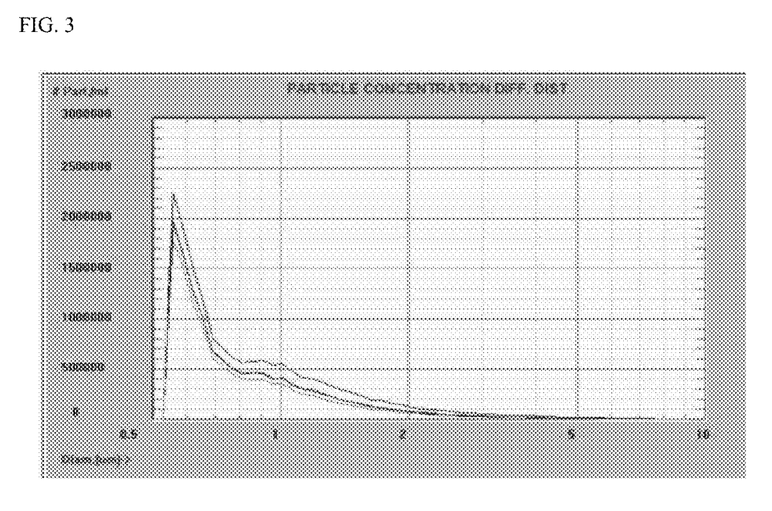
FIG. 3 is a graph illustrating particle size distributions (PSD) of the 1.05 μm sample over the duration of the experiment. Each curve represents a PSD at a given ultrasound exposure time.
Figure 4:
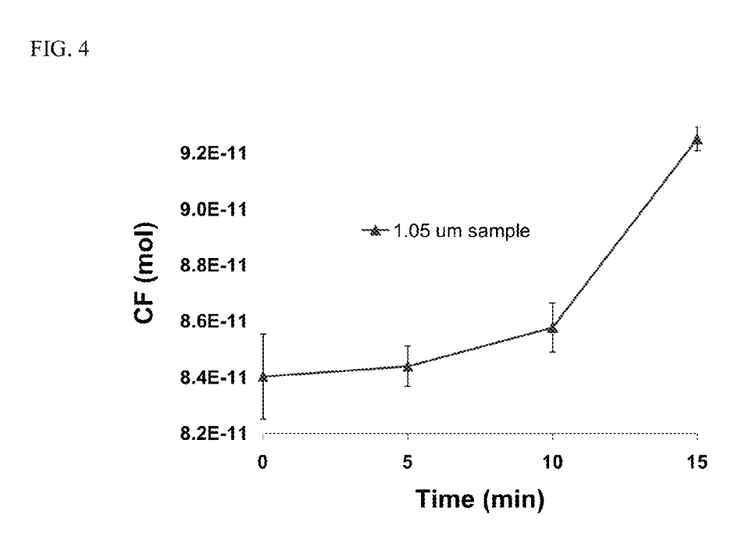
FIG. 4 is a graph illustrating free CF (mol) in solution over ultrasound exposure time in the 1.05 μm sample. Error bars represent standard error of the mean.
Figure 5:
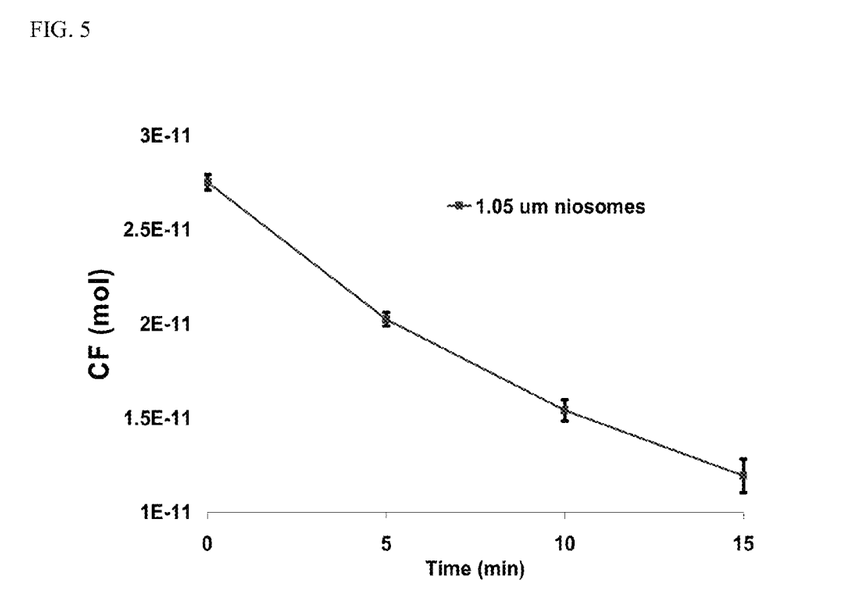
FIG. 5 is a graph illustrating encapsulated CF (mol) in 1.05 μm niosomes over ultrasound exposure time.

In FIG. 3 the PSD of the niosome sample exposed to ultrasound is shown. The slight downward shifts of the curves with successive sample measurements indicate the decrease in the overall counts over the exposure time. The overall decrease in particle counts with exposure to ultrasound in the sample was 13% as calculated by the change in total particles measured. The graph in FIG. 4 shows an increase in the CF in the suspending solution. The magnitude of this increase is greater than the relatively small shift of overall particle concentration shown in the PSD of the same sample. FIG. 5 shows the decrease in encapsulated CF with ultrasound exposure time.

Discussion

Release of CF from the niosomes after exposure to ultrasound is evidenced by the two fold decrease in encapsulated CF and the nearly 10% increase of dye measured in the suspending solution. The PSD of the vesicles shows that significant release took place with relatively low destruction of vesicles. These data support the principle that clinical levels of ultrasound may be used to disrupt the membranes of encapsulating drug vesicles and allow control of destruction and release. Studies of the exposure of non ionic surfactant vesicles to clinical levels of ultrasound showed enhanced release of encapsulated materials without corresponding levels of vesicle destruction.

The disclosure of all publications cited above are expressly incorporated herein by reference, each in its entirety, to the same extent as if each were incorporated by reference individually.

It will be seen that the advantages set forth above, and those made apparent from the foregoing description, are efficiently attained and since certain changes may be made in the above construction without departing from the scope of the invention, it is intended that all matters contained in the foregoing description or shown in the accompanying drawings shall be interpreted as illustrative and not in a limiting sense.

It is also to be understood that the following claims are intended to cover all of the generic and specific features of the invention herein described, and all statements of the scope of the invention which, as a matter of language, might be said to fall therebetween. Now that the invention has been described,

What is claimed is:

1. A method for the targeted delivery of a pharmaceutical compound to a region of a patient comprising the steps of:
   providing a niosome comprising the compound;
   administering to the patient an effective amount of the niosome wherein the niosome is administered through a catheter having an injection port; and
   inducing substantially nondestructive membrane permeabilization and controlled release of the compound in the targeted region by exposing vesicles to clinical levels of ultrasound at a frequency of between about 4 MHz and about 55 MHz.

2. The method of claim 1 further comprising the steps of monitoring the niosomes using ultrasound to determine the presence of the niosome in the target region.

3. The method of claim 1 wherein the compound is selected from the group consisting of therapeutic compounds and diagnostic compounds.

4. The method of claim 1 wherein the catheter is attached to an ultrasound probe.

5. The method of claim 1 wherein the niosome comprises polyoxyethylene sorbitan monostearate (Tween 61), cholesterol and dicetyl phosphate.

6. The method of claim 5 wherein the polyoxyethylene sorbitan monostearate (Tween 61) and the cholesterol are present in about equimolar combination.

7. The method of claim 6 wherein the niosomes are synthesized in about 1.00:1.00:0.105 molar ratio for polyoxyethylene sorbitan monostearate (Tween 61):cholesterol:dicetyl phosphate.

8. The method of claim 1 wherein the niosome is synthesized using a thin film hydration methodology.

9. A method for the targeted delivery of a compound of interest to a region of a patient comprising the steps of:
providing a niosome comprising the compound;
providing a catheter comprising in combination an ultrasound probe and an injection port;
administering to the patient an effective amount of the niosome using the catheter wherein the niosome is delivered to the site through the injection port of the catheter; and
inducing substantially nondestructive membrane permeabilization and controlled release of the compound in the targeted region by exposing vesicles to clinical levels of ultrasound at a frequency of between about 4 MHz and about 55 MHz.

10. The catheter according to claim 9 wherein the ultrasound probe has imaging capabilities to facilitate the imaging of the delivery site.

11. The method of claim 9 further comprising the steps of monitoring the niosomes using ultrasound to determine the presence of the niosome in the target region.

12. The method according to claim 11 wherein the ultrasound is used to facilitate release of a drug at the site of an atherosclerotic plaque.

13. The method according to claim 11 wherein the niosome comprises an antibody or antibody fragment to facilitate adhesion to the site of an atherosclerotic plaque.

14. The method of claim 9 wherein the compound is selected from the group consisting of therapeutic compounds and diagnostic compounds.

15. The method according to claim 9 wherein the niosome comprises an antibody or antibody fragment to facilitate adhesion to the site of interest.

16. The method according to claim 9 wherein the region of interest is an atherosclerotic plaque.

* * * * *